(12) United States Patent
Shi et al.

(10) Patent No.: US 10,426,807 B2
(45) Date of Patent: Oct. 1, 2019

(54) BONE AND JOINT PROTECTION COMPOSITION AND USE THEREOF

(71) Applicant: INFINITUS (CHINA) COMPANY LTD., Jiang Men, Guangdong (CN)

(72) Inventors: Bin Shi, Jiang Men (CN); Xiaolei Guo, Jiang Men (CN); Chung Wah Ma, Jiang Men (CN); Wei Zhang, Jiang Men (CN); Zhen Luo, Jiang Men (CN)

(73) Assignee: INFINITUS (CHINA) COMPANY LTD., Jiang Men, Guangdong (CN)

( * ) Notice: Subject to any disclaimer, the term of this patent is extended or adjusted under 35 U.S.C. 154(b) by 358 days.

(21) Appl. No.: 15/209,724

(22) Filed: Jul. 13, 2016

(65) Prior Publication Data

US 2017/0014462 A1 Jan. 19, 2017

(30) Foreign Application Priority Data

Jul. 14, 2015 (CN) .......................... 2015 1 0412697

(51) Int. Cl.
| | | |
|---|---|---|
| *A61K 36/48* | (2006.01) | |
| *A61K 36/00* | (2006.01) | |
| *A61K 36/481* | (2006.01) | |
| *A61K 38/39* | (2006.01) | |
| *A61K 31/7008* | (2006.01) | |
| *A61K 31/737* | (2006.01) | |
| *A61K 36/21* | (2006.01) | |
| *A61K 36/236* | (2006.01) | |
| *A61K 36/46* | (2006.01) | |
| *A61K 36/23* | (2006.01) | |

(52) U.S. Cl.
CPC ........ *A61K 36/481* (2013.01); *A61K 31/7008* (2013.01); *A61K 31/737* (2013.01); *A61K 36/21* (2013.01); *A61K 36/23* (2013.01); *A61K 36/236* (2013.01); *A61K 36/46* (2013.01); *A61K 38/39* (2013.01)

(58) Field of Classification Search
None
See application file for complete search history.

(56) References Cited

U.S. PATENT DOCUMENTS

| 6,019,971 A * | 2/2000 | Weiner ................. A61K 38/39 424/184.1 |
| 2006/0110468 A1* | 5/2006 | Liu ....................... A61K 36/59 424/725 |
| 2008/0003258 A1* | 1/2008 | Marcum ............... A61K 31/715 424/426 |

FOREIGN PATENT DOCUMENTS

CN 102293738 A * 12/2011

OTHER PUBLICATIONS

International Search Report.
Xiaping Weng et al:"Achyranthes bidentata polysaccharides activate the Wnt/β-catenin signaling pathway to promote chondrocyte proliferation", International Journal of Molecular Medicine, vol. 34, No. 4, Jul. 29, 2014 (Jul. 29, 2014), pp. 1045-1050.
Qian-Qian Liang et al:"Protective Effect of Ligustrazine on Lumbar Intervertebral Disc Degeneration of Rats Induced by Prolonged Upright Posture", Evidence-Based Complementary and Alternative Medicine, vol. 2014, Jan. 1, 2014 (Jan. 1, 2014), pp. 1-9.
Ken Zheng et al:"Ferulic Acid Enhances the Chemical and Biological Properties of Astragali Radix: A Stimulator for Danggui Buxue Tang, an Ancient Chinese Herbal Decoction", Planta Medica, vol. 80, No. 02/03, Jan. 31, 2014 (Jan. 31, 2014), pp. 159-164.
Wei-Tai Shih et al:"Prescription Patterns of Chinese Herbal Products for Osteoporosis in Taiwan: A Population-Based Study", Evidence-Based Complementary and Alternative Medicine, vol. 2012, Jan. 1, 2012 (Jan. 1, 2012), pp. 1-6.
First Office Action dated Jul. 26, 2018 for European patent application No. 16179138.9, 6 pages.

* cited by examiner

*Primary Examiner* — Michael Barker
*Assistant Examiner* — Randall Winston
(74) *Attorney, Agent, or Firm* — Yue(Robert) Xu; Apex Attorneys at Law, LLP

(57) ABSTRACT

The invention relates to a bone and joint protection composition and use thereof. According to the composition, the four Chinese medicinal herbs Eucommiae Cortex, Achyranthis Bidentatae Radix, Astragali Radix and Chuanxiong Rhizoma are used, and the effects of enhancing the bone density, preventing and relieving osteoporosis, restraining the activity of osteoclast, promoting the function of bone cells, increasing the formation of calcified bone, promoting cartilage repair, delaying joint recession and repairing joint damage are achieved through multiple approaches and multiple levels. On the basis, by adding glucosamine hydrochloride, chondroitin sulfate and/or collagen, the bone density can be enhanced, the osteoporosis can be prevented and treated; the activity of the osteoclast can be restrained, the function of bone cells can be promoted, the formation of calcified bone can be increased, the cartilage repair can be promoted, joint recession can be delayed, and the joint damage can be repaired.

5 Claims, No Drawings

BONE AND JOINT PROTECTION COMPOSITION AND USE THEREOF

CROSS REFERENCE OF RELATED APPLICATIONS

The present application claims the priority of Chinese Patent Application No. 201510412697.8, as filed on Jul. 14, 2015 and titled with "A bone and joint protection composition and use thereof", and the disclosure of which is incorporated herein by reference.

FIELD

The present invention relates to the pharmaceutical field, in particular to a bone and joint protection composition and use thereof.

BACKGROUND

China is entering the ranks of the world's aging countries, the incidence of osteoporosis and osteoarthritis continues to rise. At present, the preliminary investigation in China reveals that the incidence of osteoarthritis is 3%, i.e. 36 million patients, which is similar to the incidence in the United States. There are 90 million patients with osteoporosis, accounting for 7.1% of the total population. It is expected that by 2050, the number of patients will be increased to 220 million; more than half of the cases of osteoporotic fractures in the word will occur in Asia by then, wherein the absolute majority of the cases is in China. In order to protect bone and joint, delay osteoporosis and joint aging process, reduce the risk of bone fracture and osteoarthritis, prevention in early stage should be conducted.

In traditional Chinese medicine, there is no disease name like "osteoporosis", "osteoarthritis". However, according to its pathogenesis and clinical manifestation, it is very similar to "withered bone", "atrophic debility of bones", "heumatism" and "bone erosion", etc. that described in literatures of traditional Chinese medicine. Theory of traditional Chinese medicine holds that the booms and busts of bone are closely linked to kidney, liver and spleen. Kidney stores the essence of life, which produces marrow; marrow produces bone, so bone reflects the condition of kidney. Marrow is produced by the essence of life; when the essence of life is abundant, marrow is likewise abundant; since marrow is within the bone, a person having abundant marrow has strong bones. Liver stores blood, when the blood in liver is abundant, the tendon and vessel are also robust, the bone and joint are well controlled. The spleen is the acquired foundation and the origin of qi and blood for human bodies. The spleen and stomach constitute the key position for the qi-movement, communicate the upper part and the lower part, and irrigate systemically, so as to maintain the reciprocal transformation between qi, blood, the essence of life and body fluid.

If kidney deficiency occurs, the defensive yang will become insufficient, and the barrier function will be disrupted. If liver and kidney deficiency occurs, the bone and tendon will lose support, then they will become weak and atrophic; the joint will lose flexibility, and the tendon and vessel will be obstructed; and as a result, heumatism will occur. When the healthy qi prevails within the body, the pathogenic factors can not intervene. When the pathogenic factors intervenes, the healthy qi must be insufficient. As a consequence, when liver and kidney deficiency occurs, cold-dampness may slip inside; when the cold-evil congeals the passages through which vital energy circulates, qi-stagnancy and blood stasis will occur, which further exacerbates the liver and kidney deficiency. When spleen is under siege by inner cold-dampness or the transportation function of spleen is diminished, the phlegm and dampness may generate endogenously, the acquired essence of life may be depleted of origin, the various passageways will be blocked, and the blood can not be transformed into the essence of life; as a result, the bones will be in the condition of bone atrophy due to the following reasons: the nutrient substances can not be irrigated, malnutrition due to blood-insufficiency, lack of filing due to qi-insufficiency, and the resultant failure in the production of marrow and nourishment of bone. Therefore, according to Chinese medicine theory, the proposed prescriptions which nourish liver and kidney, activate qi and blood circulation as well as invigorate spleen can be used to prevent and improve osteoporosis and osteoarthritis.

Western medicine theory believes that, as the age increases, the cell function, chemical composition, and the responses to cytokines and growth factors of articular cartilage changes accordingly, and the joints are getting older. The nerval and mechanical protection mechanisms for preventing the damage of joints are also gradually weakened. For example, the functions of muscle and peripheral nerves are declined; as a consequence, the movements of nerves and muscles are uncoordinated, the muscle strength are decreased, resulting in the fact that the joints are more prone to damage, thereby aggravating the degenerative joints, and even developing osteoarthritis. The main pathological changes of osteoporosis are the decline in content and density of bone mineral, and micro-structural disorder and destruction of bone. Although there are differences between the main pathological changes of osteoarthritis and osteoporosis, osteoarthritis and osteoporosis are all degenerative diseases, and the incidence rates thereof are all in positive correlation with increasing age, the coexistence of the two diseases often appears clinically.

Thus, it is of practical significance to provide a bone and joint protection composition.

SUMMARY

In view of this, the present invention provides a composition and use thereof. According to the composition, the four Chinese medicinal herbs *Eucommia ulmoides* (Eucommiae Cortex), *Achyranthes bidentata* (Achyranthis Bidentatae Radix) *Astragalus membranaceus* (Astragali Radix) and *Ligusticum wallichii* (Chuanxiong Rhizoma) are used in cooperation, and the effects of enhancing the bone density, preventing and/or treating osteoporosis; promoting cartilage repair, restraining the activity of osteoclast, promoting the function of bone cells, increasing the formation of calcified bone, delaying joint recession and repairing joint damage are achieved through multiple approaches and multiple levels.

To achieve the above object of the invention, the present invention provides the following technical solutions:

The present invention provides a composition comprising Eucommiae Cortex, Astragali Radix, Achyranthis Bidentatae Radix and Chuanxiong Rhizoma.

In some embodiments of the present invention, the composition comprises the following components by weight parts:

| | |
|---|---|
| Eucommiae Cortex | 2-40 parts |
| Astragali Radix | 1-30 parts |

| | |
|---|---|
| Achyranthis Bidentatae Radix | 5-40 parts |
| Chuanxiong Rhizoma | 1-30 parts. |

Eucommiae Cortex is sweet and warm, distributed to the liver and kidney, and is a key drug for the treatment of low back pain; it has the function of reinforcing liver and kidney, strengthening tendons and bones. Achyranthis Bidentatae Radix processed with wine has increased functions of reinforcing liver and kidney, benefiting the essence of life and filing the marrow as well as strengthening tendons and bones. The combination of the two drugs is oriented at warmly invigorating kidney yang, with concurrently balanced supplementation of liver and kidney, aiming at strengthening tendons and bones. Both of the two drugs are the monarch drug. The ministerial drug Chuanxiong Rhizoma is spicy, warm and releases fragrant odor. It can move upstream to the top of the head, move downstream to the sea of blood, bypass the limbs, move externally to the skin, scatter the wind and relieve pain, and is a good drug for blood-activating and qi-promoting. The adjuvant drug is a "holy drug for tonifying qi", i.e. Astragali Radix, which is sweet and warm and distributed to the lung, spleen, liver and kidney meridians. It tonifies middle-Jiao and qi and spleen, such that essence of water and grain produced by spleen and stomach can nourish the promordial qi in kidney, and then the kidney can fully play the role of dominating bone; concurrently, it can be transformed into qi and supports yang, such that qi is abundant and blood is circulating. The combination of the drugs can reinforce liver and kidney, strengthen tendons and bones, tonify qi and spleen, activate blood circulation to dissipate blood stasis, and is capable of addressing both the symptoms and root cause.

In other embodiments of the present invention, the composition further comprises glucosamine hydrochloride.

Glucosamine hydrochloride is a main component for lubricating connective tissue between the joints, and is the essential substance for repairing articular cartilage, enhancing synovial fluid viscosity and improving joint cartilage metabolism. It also soothes pain caused by arthritis, having a significant anti-inflammatory and analgesic effect.

In some embodiments of the present invention, the composition comprises the following components by weight parts:

| | |
|---|---|
| Eucommiae Cortex | 2-40 parts |
| Astragali Radix | 1-30 parts |
| Achyranthis Bidentatae Radix | 5-40 parts |
| Chuanxiong Rhizoma | 1-30 parts |
| glucosamine hydrochloride | 1-20 parts. |

In other embodiments of the present invention, the composition further comprises chondroitin sulfate.

Chondroitin sulfate is a major component for lubricating connective tissue between the joints, which directly supplements cartilage matrix, relieves cartilage degradation. It can also promote metabolic activity of cartilage cells, promote the synthesis of collagen type II, restore the secretory function of cartilage cell matrix; suppress the intra-articular hydrolase activity, and protect cartilage.

In some embodiments of the present invention, the composition comprises the following components by weight parts:

| | |
|---|---|
| Eucommiae Cortex | 2-40 parts |
| Astragali Radix | 1-30 parts |
| Achyranthis Bidentatae Radix | 5-40 parts |
| Chuanxiong Rhizoma | 1-30 parts |
| glucosamine hydrochloride | 1-20 parts. |
| chondroitin sulfate | 1-20 parts. |

In other embodiments of the present invention, the composition further comprises collagen.

Collagen is common found in bone, skin, tendon, and cornea and cartilage, intervertebral discs and vitreous body. Therefore, collagen can be used as a direct complement for the extracellular matrix of the above tissues. In addition, there are researches which show that oral administration of collagen type II can eliminate joint pain.

In some embodiments of the present invention, the composition comprises the following components by weight parts:

| | |
|---|---|
| Eucommiae Cortex | 2-40 parts |
| Astragali Radix | 1-30 parts |
| Achyranthis Bidentatae Radix | 5-40 parts |
| Chuanxiong Rhizoma | 1-30 parts |
| glucosamine hydrochloride | 1-20 parts. |
| chondroitin sulfate | 1-20 parts. |
| collagen | 1-10 parts. |

The present invention also provides use of the composition for the preparation of a medicament, food and/or health care product for increasing bone density, preventing and/or treating osteoporosis.

The present invention also provides use of the composition for the preparation of a medicament, food and/or health care product for delaying joint recession, repairing joint damage, increasing the flexibility of bone and joint.

According to the composition of the present invention, the four Chinese medicinal herbs Eucommiae Cortex, Achyranthis Bidentatae Radix, Astragali Radix and Chuanxiong Rhizoma are used in cooperation, and the effects of enhancing the bone density, preventing and/or treating osteoporosis; promoting cartilage repair, restraining the activity of osteoclast, promoting the function of bone cells, increasing the formation of calcified bone, delaying joint recession and repairing joint damage are achieved through multiple approaches and multiple levels.

On the basis, by adding glucosamine hydrochloride, chondroitin sulfate and/or collagen, the bone density can be obviously enhanced, the osteoporosis can be prevented and/or treated; the effects of significant promoting cartilage repair, restraining the activity of osteoclast, promoting the function of bone cells, increasing the formation of calcified bone, delaying joint recession and repairing joint damage are achieved.

DETAILED DESCRIPTION

The present invention discloses a composition and use thereof, and a person skilled in the art can realize the present invention by referring to the contents herein and modifying the process parameters appropriately. Of particular note is that all of the similar substitutions and modifications are obvious to a person skilled in the art, and they are deemed to be included in the present invention. The method and use of the present invention are described by means of the preferred Examples. The relevant persons can obviously realize and use the technology of the present invention by modifying or appropriately altering and combining the method and use described herein without departing from the content, spirit and scope of the present invention.

The bone and joint protection composition provided by the present invention may be formulated into a variety of pharmaceutically acceptable dosage forms such as capsules, tablets, powders or granules and the like by conventional process. The present invention is not limited thereto.

The raw materials and reagents used in the composition and use thereof provided by the present invention are commercially available.

Hereinafter, the present invention is further illustrated by combining the Examples:

Example 1

Weigh accurately Eucommiae Cortex 40 g, Achyranthis Bidentatae Radix 40 g, Astragali Radix 30 g, Chuanxiong Rhizoma 30 g, glucosamine hydrochloride 1 g, chondroitin sulfate 1 g, collagen 1 g, and mix them together.

Example 2

Weigh accurately Eucommiae Cortex 30 g, Achyranthis Bidentatae Radix 30 g, Astragali Radix 25 g, Chuanxiong Rhizoma 10 g, glucosamine hydrochloride 2 g, chondroitin sulfate 2 g, collagen 2 g, and mix them together.

Example 3

Weigh accurately Eucommiae Cortex 20 g, Achyranthis Bidentatae Radix 24 g, Astragali Radix 15 g, Chuanxiong Rhizoma 7 g, glucosamine hydrochloride 2 g, chondroitin sulfate 3 g, collagen 4 g, and mixm together.

Example 4

Weigh accurately Eucommiae Cortex 21 g, Achyranthis Bidentatae Radix 40 g, Astragali Radix 20 g, Chuanxiong Rhizoma 10 g, glucosamine hydrochloride 14 g, chondroitin sulfate 10 g, collagen 20 g, and mix them together.

Example 5

Weigh accurately Eucommiae Cortex 21 g, Achyranthis Bidentatae Radix 30 g, Astragali Radix 40 g, Chuanxiong Rhizoma 15 g, glucosamine hydrochloride 20 g, chondroitin sulfate 50 g, collagen 10 g, and mix them together.

Example 6

Weigh accurately Eucommiae Cortex 2 g, Astragali Radix 30 g, Achyranthis Bidentatae Radix 5 g, Chuanxiong Rhizoma 30 g, glucosamine hydrochloride 1 g, chondroitin sulfate 10 g, collagen 10 g, and mix them together.

Example 7

Weigh accurately Eucommiae Cortex 40 g, Astragali Radix 1 g, Achyranthis Bidentatae Radix 22 g, Chuanxiong Rhizoma 16 g, glucosamine hydrochloride 20 g, chondroitin sulfate 20 g, collagen 1 g, and mix them together.

Example 8

Weigh accurately Eucommiae Cortex 20 g, Astragali Radix 16 g, Achyranthis Bidentatae Radix 40 g, Chuanxiong Rhizoma 1 g, glucosamine hydrochloride 11 g, chondroitin sulfate 1 g, collagen 5 g, and mix them together.

Example 9

Weigh accurately Eucommiae Cortex 2 g, Astragali Radix 30 g, Achyranthis Bidentatae Radix 5 g, Chuanxiong Rhizoma 30 g, and mix them together.

Example 10

Weigh accurately Eucommiae Cortex 40 g, Astragali Radix 1 g, Achyranthis Bidentatae Radix 22 g, Chuanxiong Rhizoma 16 g, and mix them together.

Example 11

Weigh accurately Eucommiae Cortex 20 g, Astragali Radix 16 g, Achyranthis Bidentatae Radix 40 g, Chuanxiong Rhizoma 1 g, and mix them together.

Example 12

Weigh accurately Eucommiae Cortex 2 g, Astragali Radix 30 g, Achyranthis Bidentatae Radix 5 g, Chuanxiong Rhizoma 30 g, glucosamine hydrochloride 1 g, and mix them together.

Example 13

Weigh accurately Eucommiae Cortex 40 g, Astragali Radix 1 g, Achyranthis Bidentatae Radix 22 g, Chuanxiong Rhizoma 16 g, glucosamine hydrochloride 20 g, and mix them together.

Example 14

Weigh accurately Eucommiae Cortex 20 g, Astragali Radix 16 g, Achyranthis Bidentatae Radix 40 g, Chuanxiong Rhizoma 1 g, glucosamine hydrochloride 11 g, and mix them together.

Example 15

Weigh accurately Eucommiae Cortex 2 g, Astragali Radix 30 g, Achyranthis Bidentatae Radix 5 g, Chuanxiong Rhizoma 30 g, glucosamine hydrochloride 1 g, chondroitin sulfate 10 g, and mix them together.

Example 16

Weigh accurately Eucommiae Cortex 40 g, Astragali Radix 1 g, Achyranthis Bidentatae Radix 22 g, Chuanxiong Rhizoma 16 g, glucosamine hydrochloride 20 g, chondroitin sulfate 20 g, and mix them together.

Example 17

Weigh accurately Eucommiae Cortex 20 g, Astragali Radix 16 g, Achyranthis Bidentatae Radix 40 g, Chuanxiong Rhizoma 1 g, glucosamine hydrochloride 11 g, chondroitin sulfate 1 g, and mix them together.

Example 18 Comparative Example

Comparative Example 1

Weighting Astragali Radix 30 g, Chuanxiong Rhizoma 40 g, glucosamine hydrochloride 1 g, chondroitin sulfate 1 g, collagen 1 g, and mix them together.

Comparative Example 2

Weighting Epimedii Folium 3 g, Lycii Fructus 3 g, Astragali Radix 30 g, Chuanxiong Rhizoma 30 g, glucosamine hydrochloride 1 g, chondroitin sulfate 1 g, collagen 1 g, and mix them together.

Bone and Joint Protection Test

Experiment 1 Animal Efficacy Test of Increasing Bone Density and Preventing Osteoporosis 1 Experimental Samples 1.1 Experimental group: the composition of the present invention: the composition provided by Example 9; batch number: 0816; dose recommended for adults: 2.88 g/d.

Low-dose sample group: the amount by oral gavage for rats per day corresponds to 10 times of the dose recommended for adults (converted to dose per kg Bw), i.e., 0.048 g/100 g.

High-dose sample group: the amount by oral gavage for rats per day corresponds to 30 times of the dose recommended for adults (converted to dose per kg Bw), i.e., 0.144 g/100 g.

1.2 The control group: Comparative Example samples: the composition of Comparative Example 1, Comparative Example 2; dose recommended for adults and the amount by oral gavage for rats are the same as those of the experimental group.

Positive control and dose: estradiol valerate tablets, manufacturer: Bayer Healthcare Co., Ltd. (Guangzhou Branch), batch number: J20130009, specification: 0.1 g/tablet, the amount by oral gavage for rats per day is 0.1 mg/100 g.

2 Reagents and Instruments

Main instruments: PUT electronic balance (Shenzhen Amput Electronic Technology Co. Ltd), mettler Toledo p1303, A4 atomic absorption spectrometer (Thermo Fisher Scientific Inc., USA).), DXA Prodigy Bone Densitometer (GE Lunar, USA), DHG-9053 Electric thermostatic air dry oven (Shanghai Sanfa Scientific Instrument Co., Ltd.); DZF-6020 vacuum drying oven (Shanghai keelrein instruments Co., Ltd.), Fixed cage, surgical instruments, syringes, etc.

Main reagents: nitric acid (guarantee reagent, Guangzhou Chemical Reagent Factory); disodium ethylenediamine tetraacetate (Guangzhou Chemical Reagent Factory); calcium standard solution (1000 ug/ml 5% HCl medium), purchased from General Research Institute of China National Steel Material Test Center.

3 Experimental Animals

SD rats in SPF grade, female, weeks of age at the time of purchasing: about 6 weeks old, weighing 220-250 g.

4 Statistical Processing of Experimental Results

Analysis of variance was adopted: firstly, test of homogeneity of variances was conducted, and F value was calculated. F value<$F_{0.05}$ indicates that there is no significant difference between the mean of each group; F value≥$F_{0.05}$, P≤0.05, a pairwise comparison method directed against the means of multiple experimental groups and one control group was used for conducting statistics; data of non-normality or uneven variance were subjected to appropriate variable conversion, and the data post conversion were subjected to statistics upon satisfying the requirements of normality or homogeneity of variance; if the requirements of normality or homogeneity of variance were still unsatisfied after variable conversion, rank sum test would be used for statistics.

5 Experimental Methods and Results 5.1 Experimental Method

The methods in "Technical specifications for inspection and evaluation of health food (2003 edition)" was adopted. SD Rats weighing 220-250 g were adopted and maintained under normal feed, quarantine and observation in the experimental environment (barrier systems) for three days. The rats were anesthetized by intraperitoneal injection of 350 mg/kg BW of chloral hydrate solution. After abdominal fixation, the hairs at medioventral line which are 3-4 cm away from the vaginal opening were removed. The skin was sterilized with tincture of iodine and alcohol. Upon slight drying, the skin and abdominal muscle were incised by 2-3 cm. White fat was visible over the incision horizon. After poking away the fat layer, the uterus was found. The uterine horn at one side was gently pulled out; at its end, an ovary enveloped by fat mass was visible. Upon separation of fat mass, the ovary in pink or yellowish red color can be seen. The ovary was clipped by a hemostatic clamp, and the fallopian tube below the ovary (including fat) was ligated with a silk thread. The ovary was cut off (checking whether it was completely cut off), and the uterine horn was returned back to the abdominal cavity by the way. The ovary at the other side was cut off by the same method. After the suture of abdominal muscles and skin layer by layer, re-sterilization was conducted. Finally, 20,000 U penicillin was injected intramuscularly. Oophorectomy may also be operated via the incision at costovertebral angle of the back. To ensure successful operation, rats were subjected to vaginal smear check (a small amount of physiological saline was drawn with a pipette, which was gently inserted into the vagina for 1-2 cm; after rinsing for several times, the rinse was drawn off, coated on the slide and investigated under microscope) on the fifth day post the removal of the ovaries (once a day for consecutive 5 days) so as to check whether the ovaries of the rats were completely removed. The smears showing estrous reaction (a large number of semi-transparent, flat epidermal cells were seen under microscope) indicated that the ovaries of the animals were not completely removed; under such circumstances, the animals should be discarded. The sham operation group was composed of 12 rats that are not ovariectomized. The other trial drug groups, which were composed of rats that were screened post surgical operation to be successful in the oophorectomy, were observed for 3 days under normal conditions and then randomly divided into 8 groups (12 rats per group): model control group, positive control group, low-dose sample group, high-dose sample group. The sham operation group and model group were given distilled water per day by oral gavage, the rest of the sample groups were given corresponding doses of the test drug samples (one feeding per day for three months).

5.2 Observed Indicators 5.2.1 Observation of the General State

Animals were observed daily for status (exterior signs, behaviors, fecal property, feeding conditions, etc.). And the animals were weighed one week after each feeding to observe the growth condition.

5.2.2 Determination of Bone Calcium 5.2.2.1 Sample Collection and Measurement of Bone Calcium The determination was conducted by means of atomic absorption flame photometry with the following parameters: the flow rate of the burning acetylene gas was 1.4 ml, the flame height was 8.6 cm, the detection wavelength was 422 nm; the femora of the rats at one side were dried to constant weight at a 105° C. oven, then weighted for dry weight; after weighting, the leg bones of the rats were dissolved with nitric acid and diluted to 10 ml, from which 0.10 ml was extracted, and diluted 700-fold with 0.02M ethylenediamine tetraacetic acid solution to subject to sample analysis.

5.2.2.2 Determination of Bone Density

The femora at both sides were measured for bone density with a Prodigy DXA Bone Densitometer. The femora at both sides were positioned for measurement.

5.3 Experimental Results 5.3.1 Observation of the General State

Compared with the sham operation group, animals from feeding and modeling groups had slightly less smooth hairs, but there was no significant difference in terms of other exterior signs, behaviors, fecal property, etc. Compared with the model control group, the test sample group, Comparative Example 1 group, Comparative Example 2 group and the positive control group did not have significant difference in terms of exterior signs, behaviors, fecal property, etc.

As for the body weight, after feeding for 12 weeks, the body weights of animals from test sample, Comparative Example 1, Comparative Example 2 and the positive control groups were significantly higher than those of the sham operation group, but lower than those of the model group.

5.3.3 Effect on Bone Calcium Content and Bone Density of Left Femora in Rats

TABLE 1

Effect on bone calcium content and bone density of left femora in rats ($\bar{x} \pm$ s.d., N = 12)

|  | Groups | bone density BMD (g/cm$^3$) | bone calcium content (mg/g) |
|---|---|---|---|
| Control group | sham operation group | 0.212 ± 0.008 | 193.9 ± 38.8 |
|  | model group | 0.195 ± 0.010# | 135.4 ± 24.8# |
|  | positive control group | 0.207 ± 0.010** | 178.2 ± 29.3** |
|  | Comparative Example 1 low-dose group | 0.197 ± 0.013 | 138.3 ± 30.2 |
|  | Comparative Example 1 high-dose group | 0.199 ± 0.011 | 141.0 ± 28.8 |
|  | Comparative Example 2 low-dose group | 0.198 ± 0.009 | 140.8 ± 28.3 |
|  | Comparative Example 2 high-dose group | 0.200 ± 0.009* | 145.1 ± 19.9 |
| Experimental group | test sample (Example 9) low-dose group | 0.202 ± 0.011* | 166.2 ± 19.7* |
|  | test sample (Example 9) high-dose group | 0.204 ± 0.008* | 167.3 ± 20.4* |

Note:
denotes P < 0.01 versus the sham operation group;
*denotes P < 0.05 versus the model group,
**denotes P < 0.01 versus the model group.

Table 1 shows that, compared with the sham operation group, the femoral bone density values and bone calcium contents of the model group were significantly decreased, suggesting that the rat osteoporosis model was successfully established.

Compared with the model group, the bone density values of low-dose sample groups and high-dose sample group were significantly higher (P<0.05), and the bone calcium contents were also significantly increased (P<0.05). The bone density and bone calcium content values of positive control group were also significantly higher than those of the model group (P<0.01).

Compared with the model group, the bone calcium contents and bone density values of Comparative Example 1 group have the rising trend, but without statistical difference (P>0.05). The bone density values of Comparative Example 2 high-dose group were significantly increased (P<0.05), but the bone calcium contents only had the rising trend (P>0.05).

Compared with the positive control group, the femoral bone density values and bone calcium contents of test sample high-dose group and low-dose group were significantly decreased (P<0.01); compared with Comparative Example 1 high- and low-dose groups, both of the femoral bone density values and bone calcium contents of test sample high-dose group and low-dose group were significantly increased (P<0.05); compared with Comparative Example 2 low-dose group, both of the femoral bone density values and bone calcium contents of test sample high- and low-dose groups were significantly increased (P<0.05); compared with Comparative Example 2 high-dose group, both of the femoral bone density values and bone calcium contents of test sample high-dose group were significantly increased (P<0.05).

The above data showed that, the samples have the effects of elevating bone calcium content and increasing bone density, and can be used to relieve osteoporosis, whereas Comparative Example 1 and Comparative Example 2 do not have obvious effect of relieving osteoporosis.

The effect of relieving osteoporosis of high-dose sample groups is superior to that of Comparative Example 1 high-dose group and low-dose group and Comparative Example 2 high-dose group and low-dose group. The effect of relieving osteoporosis of low-dose sample groups is superior to that of Comparative Example 1 high-dose group and low-dose group and Comparative Example 2 low-dose group. The compositions prepared by Examples 1 to 8, Examples 10 to 17 were subjected to the above experiments, and the experimental results were the same or similar as the effects of the composition prepared by Example 9 and were without significant difference (P>0.05), which shows that all of the compositions prepared by Examples 1 to 17 of the present invention have the functional effect of increasing bone density.

Experiment 2 Animal Efficacy Test of Repairing Joints

1 Experimental Samples 1.1 Experimental group: the composition of the present invention: the composition provided by Example 9; batch number: 0816; dose recommended for adults: 2.88 g/d.

Sample Dose: the amount by oral gavage for New Zealand white rabbits per day corresponds to 30 times of the dose recommended for adults (converted to dose per kg Bw), i.e., 0.144 g/100 g.

1.2 The control group: Comparative Example samples: the composition of Comparative Example 1, Comparative Example 2; dose recommended for adults and the New Zealand rabbits are the same as those of the experimental group.

Normal control group: the non-surgical group was given distilled water at same amount as other groups.

2 Reagents and Experimental Instruments

Experimental instruments: Olympus optical microscope camera system (BH-2 type); German ZEISS (Zeiss) Axiotron research microscope.

Main reagents: EDTA (Chengdu Chemical Reagent Company); paraformaldehyde (Beijing Chemical Reagent Company); AB-PAS staining reagent; papain (Sigma-Aldrich Co. LLC.) and so on.

3 Experimental Animals

Healthy New Zealand rabbits, weighing 2.5-3.0 Kg, male, fed on standard diet, accessible to food and water freely.

4 Statistical Processing of Experimental Results

Analysis of variance was adopted: firstly, test of homogeneity of variances was conducted, and F value was calculated. F value<$F_{0.05}$ indicates that there is no significant difference between the mean of each group; F value≥$F_{0.05}$, P≤0.05, a pairwise comparison method directed against the means of multiple experimental groups and one control group was used for conducting statistics; data of non-normality or uneven variance were subjected to appropriate variable conversion, and the data post conversion were subjected to statistics upon satisfying the requirements of normality or homogeneity of variance; if the requirements of normality or homogeneity of variance were still unsatisfied after variable conversion, rank sum test would be used for statistics.

5 Experimental Method and Results 5.1 Experimental Methods

According to the method disclosed in literature, the bone and joint disease model was established by injecting papain into the joint cavity of the rabbits' knees. After the rabbits were anesthetized with sodium pentobarbital (30 mg/kg, intravenous injection), the hairs around the knee joint of the left hind leg were shaved. The knee joint was slightly bent, and then 0.3 ml of 4% papain solution in physiological saline was injected into the rabbits' knee joint cavity through patellar ligament (injected at both sides of the joint) for once every 3 days. The injections were implemented for consecutive 3 times (note: New Zealand rabbits from normal control group do not need to have this operation). Two weeks after the completion of the last injection of papain, the administration of samples were started. The samples were administrated for consecutive 6 weeks (the model group and normal control group were consecutively administered with distilled water), the rabbits in each group were all sacrificed, then the knee joints from the normal control group and the inner femora at the left knee joints from the rest of modeling groups were cut off by means of a sharp blade to generally observe the conditions of synovium and cartilage by naked eyes. Using cartilage AB-PAS staining, the morphological structure of articular cartilage and change of coloration of proteoglycan in cartilage matrix were observed under light microscope. Using modified histology—histochemical grading system (HHGS), the articular cartilages from each of the specimens were subjected to pathological grading and scoring.

5.2 Observed Indicators 5.2.1 Observation of the General State

Animals were observed daily for status (exterior signs, behaviors, fecal property, feeding conditions, etc.). And the animals were weighed weekly.

5.2.2 Observation of the Cartilage 5.3 Experimental Results 5.3.1 Observation of the General State During the duration of the experiment, it was seen that the New Zealand rabbits from the normal group had good mental state, and had no abnormal changes in hair color. However, the New Zealand rabbits from each of the modeling groups had claudication in varying degrees and significantly reduced spontaneous activities as well as significantly affected knee joint movements.

As for the body weight, after feeding for 12 weeks, the body weights of animals from Comparative Example 1, Comparative Example 2 and the positive control groups were significantly lower than those of the normal control group, but higher than those of the model group.

5.3.2 Observation of the Cartilage

The appearance of the joint cartilages of rabbits' knees from the normal group was in bright blue-white color; was free from cracks, softening or defects; and was rigid upon touch. The amount of synovial fluid was small, and the texture of the synovial fluid was clear and transparent. 8 weeks after modeling, the knee joints of each group were injured seriously. The manifestations included: the faces of the joint cartilage were significantly uneven, or even the cartilages had intermittent cracks and defects. Among these, the cartilage situations of the model group were more serious than the other groups.

Upon AB-PAS staining, the acidic mucopolysaccharides in cartilage matrix were in blue color, whereas the neutral mucilage substances were in red color. The AB-PAS staining of normal group showed that the cartilage staining was clear and uniform and was without the phenomenon of loss of staining; the chondrocytes were distributed evenly and without the clustering of chondrocytes; the surface layer of the cartilage was smooth and flat. 8 weeks after modeling, it could be seen that the surface layer of the cartilage from the model group had the phenomenon of loss of staining, the staining was not uniform, and the surface of the cartilage was uneven. It could also be seen that, as for the rest of the various sample groups, the cartilage staining was uneven and ambiguous, the morphology of the chondrocytes and matrix was unclear, and the surface layer and middle layer or even the deep layer had a large amount of unstained area, concurrently with varying degrees of cartilage cracks or defects. The scoring are as follows:

TABLE 2

The comparative table for AB-PAS staining pathological scores ($\bar{x}$ ± s.d., N = 6)

| groups | | AB-PAS scores |
|---|---|---|
| Control group | Model group | 11.30 ± 0.91# |
| | Normal control group | 0.55 ± 0.61 |
| | Comparative Example 1 group | 10.77 ± 1.07 |
| | Comparative Example 2 group | 10.38 ± 0.95 |
| Experimental group | test sample group | 8.85 ± 0.81* |

Notes:
denotes P < 0.05 versus normal control group;
*denotes P < 0.05 versus model group.

Compared with the model group, the pathological scores of the experimental group were decreased compared with the model group (P<0.05); Comparative Example 1 and Comparative Example 2 groups had the descending trend but no significant difference (P>0.05). Compared with the normal control group, Comparative Example 1 group and Comparative Example 2 group, the experimental group had a significant difference (P<0.05). This fact indicates that the experimental group can elevate the proteoglycan content of cartilage matrix and promote joint repair, but the Comparative Example 1 group and Comparative Example 2 group do not have this effect. Moreover, the effect of the experimental group is superior to those of the Comparative Example 1 group and Comparative Example 2 group.

The compositions prepared by Examples 1 to 8, Examples 10 to 17 were subjected to the above experiments, and the experimental results were the same or similar as the effects of the composition prepared by Example 9 and were without significant difference ($P>0.05$), which shows that all of the compositions prepared by Examples 1 to 17 of the present invention have the functional effect of improving joint movement capacities.

The above are only preferred embodiments of the present invention, and it should be noted that, a person having ordinary skill in the art can also make improvements and modifications thereto without departing from the principles of the present invention, and these improvements and modifications should also be considered as falling within the scope of the present invention.

What is claimed is:

1. A bone and joint protection composition, characterized in that it consists of the following components by weight parts:

| | |
|---|---|
| Eucommiae Cortex | 2-40 parts |
| Astragali Radix | 1-30 parts |
| Achyranthis Bidentatae Radix | 5-40 parts |
| Chuanxiong Rhizoma | 1-30 parts |
| glucosamine hydrochloride | 1-20 parts. |

2. A bone and joint protection composition, characterized in that it consists of the following components by weight parts:

| | |
|---|---|
| Eucommiae Cortex | 2-40 parts |
| Astragali Radix | 1-30 parts |
| Achyranthis Bidentatae Radix | 5-40 parts |
| Chuanxiong Rhizoma | 1-30 parts |
| glucosamine hydrochloride | 1-20 parts |
| chondroitin sulfate | 1-20 parts. |

3. A bone and joint protection composition, characterized in that it consists of the following components by weight parts:

| | |
|---|---|
| Eucommiae Cortex | 2-40 parts |
| Astragali Radix | 1-30 parts |
| Achyranthis Bidentatae Radix | 5-40 parts |
| Chuanxiong Rhizoma | 1-30 parts |
| glucosamine hydrochloride | 1-20 parts |
| chondroitin sulfate | 1-20 parts |
| collagen | 1-10 parts. |

4. A method for increasing bone density and/or treating osteoporosis comprising administering to a subject in need thereof a composition according to claim 1.

5. A method for delaying joint recession, repairing joint damage, increasing the flexibility of bone and joint comprising administering to a subject in need thereof a composition according to claim 1.

* * * * *